United States Patent
Zeng et al.

(10) Patent No.: US 11,229,752 B2
(45) Date of Patent: Jan. 25, 2022

(54) PEN NEEDLE ASSEMBLY HAVING AN OUTER COVER

(71) Applicant: Becton, Dickinson and Company, Franklin Lakes, NJ (US)

(72) Inventors: Xi Zeng, Jiangsu (CN); Huasheng Huang, Jiangsu (CN); Wei Hu, Shanghai (CN); Fei Wang, Shanghai (CN); Tingting Fan, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 368 days.

(21) Appl. No.: 16/465,753

(22) PCT Filed: Dec. 5, 2017

(86) PCT No.: PCT/US2017/064706
§ 371 (c)(1),
(2) Date: May 31, 2019

(87) PCT Pub. No.: WO2018/106686
PCT Pub. Date: Jun. 14, 2018

(65) Prior Publication Data
US 2019/0388624 A1    Dec. 26, 2019

(30) Foreign Application Priority Data

Dec. 6, 2016  (CN) .......................... 201611110864.4
Dec. 6, 2016  (CN) .......................... 201621333821.8

(51) Int. Cl.
*A61M 5/32* (2006.01)
*A61M 5/00* (2006.01)

(52) U.S. Cl.
CPC ........ *A61M 5/3278* (2013.01); *A61M 5/3202* (2013.01); *A61M 5/002* (2013.01);
(Continued)

(58) Field of Classification Search
CPC .... A61M 5/002; A61M 5/347; A61M 5/3278; A61M 5/3202; A61M 5/3213;
(Continued)

(56) References Cited

U.S. PATENT DOCUMENTS

2006/0032769 A1   2/2006  Erickson et al.
2012/0037655 A1   2/2012  Dibiasi
(Continued)

FOREIGN PATENT DOCUMENTS

| AU | 2009202158 A1 | 12/2009 |
| JP | 2007-14615 A  | 1/2007  |
| JP | 2012-40386 A  | 3/2012  |

OTHER PUBLICATIONS

International Search Report dated May 8, 2018, which issued in the corresponding PCT Patent Application No. PCT/US2017/064706.

*Primary Examiner* — Manuel A Mendez
*Assistant Examiner* — Justin L Zamory
(74) *Attorney, Agent, or Firm* — Dickinson Wright PLLC (57) ABSTRACT

A needle hub assembly for coupling to a pen needle delivery device includes an outer cover having a first well receiving the needle hub and inner shield covering a cannula of the needle hub. A second well is spaced from the first well and receives the inner shield. In use, the pen delivery device is coupled to the connecting end of the needle hub to withdraw the needle hub and inner shield from the first well. The inner shield is inserted into the second well where the inner shield is gripped so that the inner shield can be separated from the needle hub without the user handling the outer cover or the inner shield. After use, the needle hub is inserted into the first well and the pen needle delivery device is separated from the needle hub. The needle hub is retained within the first well where the outer cover containing the used needle hub and inner shield can be discarded as a single unit.

19 Claims, 10 Drawing Sheets

(52) U.S. Cl.
CPC ......... *A61M 5/3204* (2013.01); *A61M 5/3205* (2013.01); *A61M 2005/3206* (2013.01); *A61M 2005/328* (2013.01)

(58) Field of Classification Search
CPC .......... A61M 5/3204; A61M 2005/328; A61M 2005/3206; A61M 2005/3215; B65D 83/02
See application file for complete search history.

(56) References Cited

U.S. PATENT DOCUMENTS

| | | |
|---|---|---|
| 2015/0034516 A1 | 2/2015 | Chapin et al. |
| 2015/0119818 A1 | 4/2015 | Evans |

PEN NEEDLE ASSEMBLY HAVING AN OUTER COVER

This application claims priority under 35 USC § 119(a) from Chinese Utility Model Application No. 201621333821.8, filed on Dec. 6, 2016, and Chinese Invention Patent Application No. 201611110864.4, filed on Dec. 6, 2016, which are hereby incorporated by reference in their entirety.

FIELD OF THE INVENTION

The present invention relates generally to a pen needle assembly having an outer cover forming an enclosure for the pen needle. More particularly, the present invention generally relates to an outer cover having a first well to retain a needle hub having an inner shield and to retain the needle hub after use to reduce the risk of inadvertent needle stick. The outer cover has a second well to receive the inner shield for separating the inner shield from the needle hub without the need to handle the inner shield.

BACKGROUND OF THE INVENTION

Insulin and other injectable medications are commonly delivered with drug delivery pens, whereby a disposable pen needle hub is attached to the pen to facilitate drug container access and allow fluid egress from the container through the needle into the patient.

Various pen needle delivery devices are known in the art for dispensing the substance to the patient. The delivery devices often use a disposable needle hub having a cannula or needle extending from a patient end of the hub for inserting into the patient. A non-patient end of the hub is coupled to the pen delivery device for delivering the substance to the patient.

The needle hub assembly is often packaged in a container containing several loose needle hubs. A needle hub is selected from the package and attached to the pen needle delivery device for injecting the patient and then removed to be discarded. The needle hub package includes an outer cover that encloses the needle hub and a removable seal that is peeled from the outer cover to open the cavity so that the needle hub can be removed. The needle hub can have a threaded non-patient end that is threaded onto the delivery device. The delivery device with the attached needle hub is then removed from the outer cover. An inner needle shield is attached to the needle hub to cover the cannula until the device is ready for use. The shield is removed to expose the cannula for use to deliver the substance to the patient. After use, the needle hub can be inserted back into the outer cover to enclose the exposed cannula. The pen delivery device is separated from the needle hub leaving the needle hub within the outer cover.

The prior devices require the use of both hands to connect to and remove the needle hub from the delivery device. During the placement back into the outer cover, the cannula is exposed and provides an increased risk of accidental needle stick. The manual operation of holding the outer cover while positioning the spent needle hub and cannula into the cavity of the outer cover can be difficult without accidental needle stick.

Existing pen needle assemblies are disclosed in U.S. Patent Application Publication Nos. 2006/0229562 to Marsh et al. and 2007/0149924 to R. Marsh, the entire contents of both of which are hereby incorporated by reference.

Although the prior devices have been suitable for the intended use, there is a continuing need in the industry for improved packaging for a pen needle hub assembly.

SUMMARY OF THE INVENTION

The present invention is directed to a pen needle assembly having an outer cover forming a package for the pen needle assembly. In particular, the invention is directed to a package or outer cover for a needle assembly that can be used in a manner to reduce the risk of inadvertent needle stick.

In one embodiment, the pen needle assembly includes an outer cover for receiving a needle hub to retain the needle hub and cannula in a sterile condition until use. The outer cover has a recess or well for receiving an inner shield that covers the cannula extending from the needle hub so that the inner shield can be removed from the needle hub without the operator handling the inner shield.

In accordance with another aspect, the inner shield can be inserted into a well in the outer cover so that the inner shield is retained by a friction fit or interference fit. The needle hub and cannula can then be pulled to separate the inner shield while the inner shield is retained in the well without the need for the user to handle the inner shield.

In accordance with another feature, the needle hub and cannula can be inserted into a needle hub well in the outer cover after use of the pen needle where the pen needle delivery device can be separated from the needle hub. The needle hub is retained in the needle hub well by a friction fit or interference fit to enclose the cannula and reduce the risk of inadvertent needle stick. The outer cover with the retained needle hub can be safely discarded.

The various features of the embodiments are basically attained by providing a package for a pen needle assembly including an outer cover receiving a needle hub having an inner shield covering a cannula on the needle hub. The outer cover has a top face and a bottom face with a configuration and dimension for contacting a supporting surface for the assembly and supporting the outer cover in an upright position. The top face of the outer cover has a first open well with a dimension to receive and store the needle hub and inner shield until ready for use. The outer cover can retain the needle hub by a friction fit or by an interference fit. The top face of the outer cover includes an inner shield well with a dimension for receiving the inner shield and retaining the inner shield after separating from the needle hub.

In one embodiment, the inner shield well has a dimension to receive the inner shield by a friction fit or interference fit so that inserting the inner shield into the well grips the inner shield with a sufficient force that the needle hub when attached to the pen needle can be pulled outward to separate the inner shield to expose the cannula for delivering a substance to a patient. After use of the needle hub and cannula, the needle hub is inserted into the needle hub well where the needle hub is gripped so that the pen needle can be separated from the needle hub without the operator handling the needle hub thereby reducing the risk of inadvertent needle stick. In one embodiment, the needle hub can be gripped by a friction fit or interference fit or by other mechanical connection to attach the used needle hub to the outer cover.

The features of the invention are further attained by providing a pen needle assembly for a pen needle delivery device, where the assembly includes an outer cover, a needle hub having a needle cannula, and an inner needle shield covering the cannula. The needle hub includes a body with a non-patient end for coupling to the pen needle delivery device where the needle hub has the cannula extending from a patient end. The inner shield is coupled to the needle hub to cover the cannula. The outer cover has bottom face with a dimension and configuration for contacting a support surface and retaining the outer cover in an upright position. The outer cover has a top face with a first well forming a needle hub well receiving the needle hub and inner shield. The top face has a second well forming an inner needle shield well with a dimension to receive the inner shield. The second well has a dimension less than the dimension of the first well. The inner shield can be received in the second well by a friction or interference fit to grip the inner shield so that the inner shield can be removed from the needle hub to expose the cannula without the need for the operator to manually remove the inner shield. After use, the needle hub can be inserted back into the first well to grip the needle hub so that the pen needle can be separated from the needle hub and the spent or used needle hub can be retained in the outer cover for disposal.

The objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components, and structures.

DETAILED DESCRIPTION OF THE EXEMPLARY EMBODIMENTS

The present invention is directed to a pen needle assembly for use with a pen delivery device. The invention is further directed to a pen needle assembly for a needle hub where the needle hub can be placed in an outer cover that forms an enclosure after use to reduce the risk of accidental needle stick.

It will be understood by one skilled in the art that this disclosure is not limited in its application to the details of construction and the arrangement of components set forth in the following description or illustrated in the drawings. The embodiments herein are capable of being modified, practiced or carried out in various ways. Features of the disclosure embodiments can be substituted features of a different embodiment, used with or combined with features of other embodiments. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The needle hub assembly can enable the convenient and easy assembly, and removal of the needle hub assembly with respect to a pen delivery device with reduced handling of the exposed needle cannula. The outer cover for the needle hub can be placed on a flat surface, such as a table, so that the pen delivery device can be attached to the needle hub with one hand thereby reducing the risk of the needle stick from handling the needle hub with the exposed needle cannula.

Figure 1:
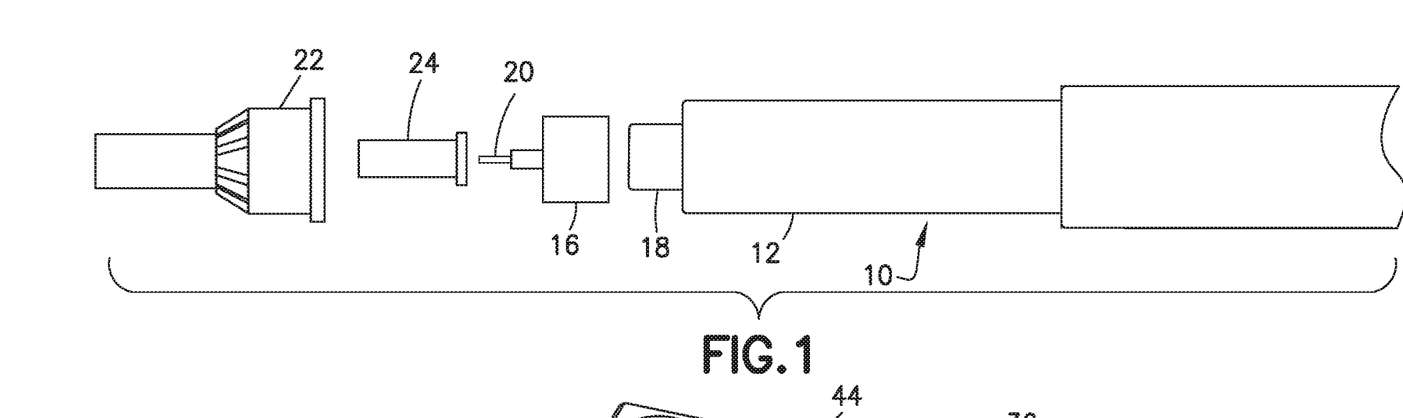
FIG. 1 is an exploded perspective view of a pen needle assembly in one embodiment showing the pen delivery device, needle hub, inner shield and cover.

Pen needle delivery device 10, as shown in FIG. 1 typically comprises a dose knob/button, an outer sleeve 12, and a cap. A dose knob/button allows a user to set the dosage of medication to be injected. The outer sleeve 12 is gripped by the user when injecting medication. The cap is used by the user to securely hold the pen injector device 10 in a shirt pocket, purse or other suitable location and provide cover/protection from accidental needle injury.

In standard pen needle delivery devices the dosing and delivery mechanisms are all found within the outer sleeve 12 and is not described in greater detail here as they are understood by those knowledgeable of the prior art. A medicament cartridge is typically attached to a standard pen injector housing via known attachment means. The distal movement of a plunger or stopper within the medicament cartridge causes medication to be forced into the reservoir housing. The medicament cartridge is sealed by a septum and punctured by a septum penetrating needle cannula located within a reservoir or housing. Reservoir housing is preferably screwed onto the medicament cartridge although other attachment means can be used. The pen needle delivery device can be a standard pen delivery device known in the industry so that the pen needle delivery device is not shown in detail.

The pen needle delivery device 10 is connected to needle hub 16 shown in FIG. 1 that is has a connecting non-patient end with internal threads that screw onto a threaded end 18 of the delivery device 10. A needle cannula 20 extends from the patient end of the needle hub 16 for delivering the substance to the patient. An outer cover 22 can be provided to cover the needle cannula to protect the patient from accidental needle stick before and after use. An inner shield 24 is provided over a post extending from the end of the needle hub 16 to enclose the cannula. During use, the needle hub 16 is connected to the pen delivery device and the inner shield is removed. After use, the outer cover is generally placed back on needle hub to cover the needle cannula. The needle hub with the cover is then removed from the pen needle delivery device and discarded.

Figure 1A:
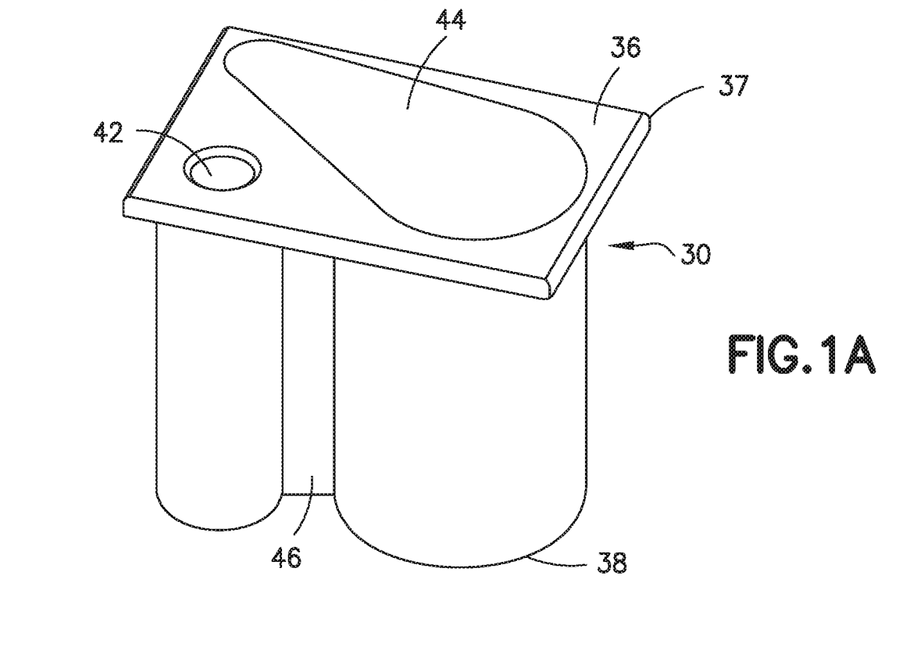
FIG. 1A is a perspective view of the outer cover for containing the needle hub assembly showing the removable seal enclosing the needle hub and the cavity for the inner shield.

In the present assembly, the pen needle delivery device is adapted for connecting to the needle hub of a pen needle assembly. The pen needle assembly includes an outer cover 30, as shown in FIG. 1A, needle hub 16, inner shield 24, and a removable seal 44. In one embodiment, the outer cover 30 forms and enclosure or a packaging system of the needle hub 16 for the pen needle assembly. Outer cover 30 forms the enclosure or packaging for the needle hub 16 during shipping and handling of the needle hub. The outer cover 30 can be a single unit as shown in FIG. 1A for a single needle hub having a single pen needle assembly. In other embodiments shown in FIGS. 2-5, the outer cover 30 can be an array 32 of a plurality of outer covers 30 each containing a single needle hub 16 to form an array of pen needle assemblies. The array 32 of pen needle assemblies and the outer covers 30 can be connected together by a frangible line 34, perforated lines or other mechanism that enable separation of the individual outer covers 30 before or after use of the pen needle. The outer cover 30 can be separated into sub-assemblies of individual pen needle assemblies as desired.

Each outer cover 30 includes a top face 36 and a bottom face 38. In one embodiment, the top face 36 is defined by a substantially flat, planar member 37. A recess forming a first well 40 with a dimension for receiving and storing a needle hub 16 and a second recess forming a second well 42 spaced to form the second well for receiving the inner shield 24 of the needle hub assembly are formed in top face 36. As shown, well 42 for inner shield 24 has a diameter less than a dimension of well 40 for needle hub 16.

A seal 44 forming a closure member as shown in FIG. 1A is attached to the top face 36 to overlie the first well 40 to enclose the needle hub assembly until ready for use. The seal 44 in one embodiment can be attached to the open end of the needle hub 16 and to the top face 36 of the outer cover to provide a sterile and clean enclosure for the cannula 20. In the embodiment shown, the seal 44 is a flexible seal attached by an adhesive, such as a heat sensitive or activated adhesive or a pressure sensitive adhesive that can be easily removed by the user at the time of use. The seal 44 is preferably a seal that is removable and can be peeled and separated from the open first well 40 and the top face by the user to expose the needle hub 16. The seal 44 can be removable or peel label. In other embodiments, the seal can be other forms of a suitable seal that is able to close the well 40 and maintain the needle hub 16 in a clean and sterile condition until use. The array 32 also has a seal 44 closing each well 40 of the outer covers 30 containing the needle hub 16. For ease of illustration, the seals 44 are not shown in FIGS. 2 and 3 although it will be understood that prior to use of the needle hub 16 each well 40 is closed by a respective seal 44 to maintain the needle hub 16 in a clean and sterile condition until ready for use. As shown, top face 36 has a recess or indicia indicating the location and position of the seal 44.

Bottom face 38 of outer cover 30 and array 32 form a substantially flat bottom configured to lay on a substantially flat surface, such as a table top, during use so that the outer cover and array are stable and able to be used in a stand-alone manner. The bottom face 38 has dimension so that the outer cover 30 and/or the array 32 are supported in an upright position. Bottom face 38 can have a textured surface or a suitable coating of a slip resistant material to inhibit sliding movement of the outer cover when placed on a supporting surface. In one embodiment, the outer cover stabilizes the assembly so that the operator can connect a needle hub assembly to the pen delivery device using one hand to reduce the risk of accidental needle stick.

Figure 18:
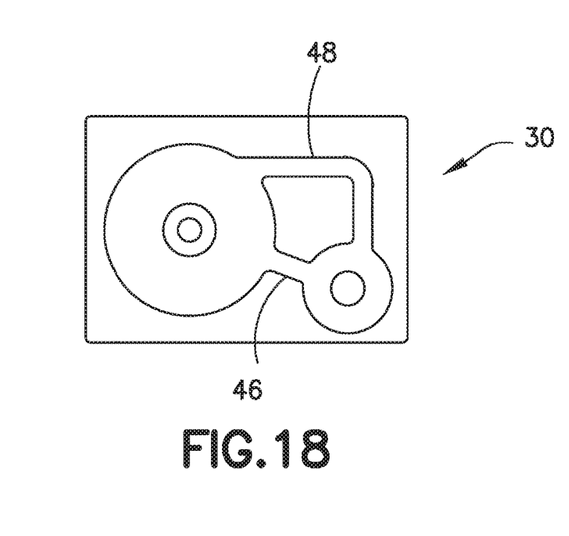
FIG. 18 is a bottom view of the outer cover.

As shown in FIG. 18, well 40 and well 42 are spaced apart from each other and have substantially the same depth to form a supporting surface. A connecting portion 46 extends directly between the well 40 and well 42. In one embodiment, a connection portion 48 extends between the well 40 and well 42 and has a substantially L-shape to assist in providing a stabilizing configuration. Each connecting portion 46 and 48 has a height corresponding to the height of well 40 and well 42 to form a supporting surface and the bottom face with a dimension able to support the outer cover 30 in an upright position. The connecting portions 46 and 48 have a bottom edge at the bottom face 38 of cover 30 to form a stabilizing surface for the cover when placed on a supporting surface. The bottom end of the connecting portions 46, 48 can also have a textured or slip-resistant material or coating.

Figure 2:
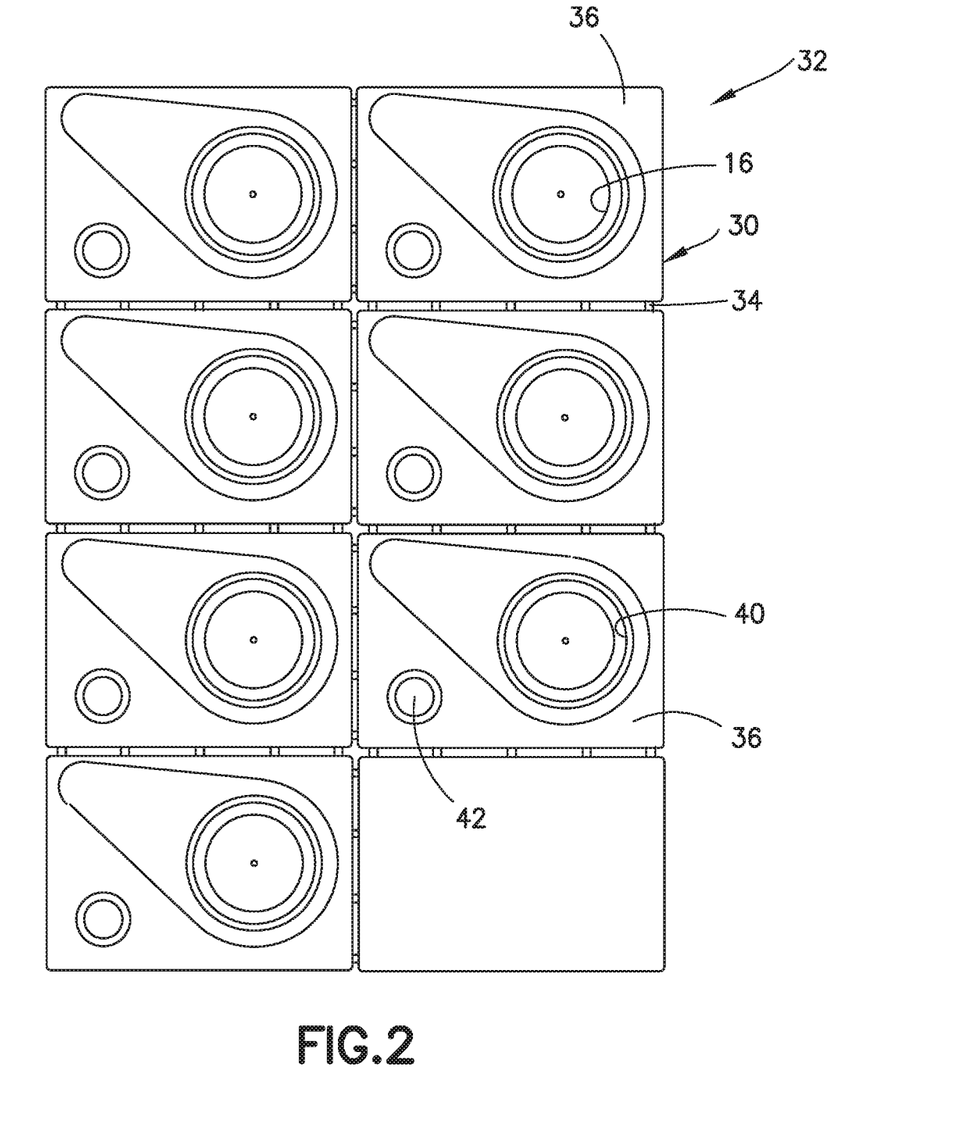
FIG. 2 is a top view of an array of needle hubs that can be separated prior to or after use.
Figure 9:
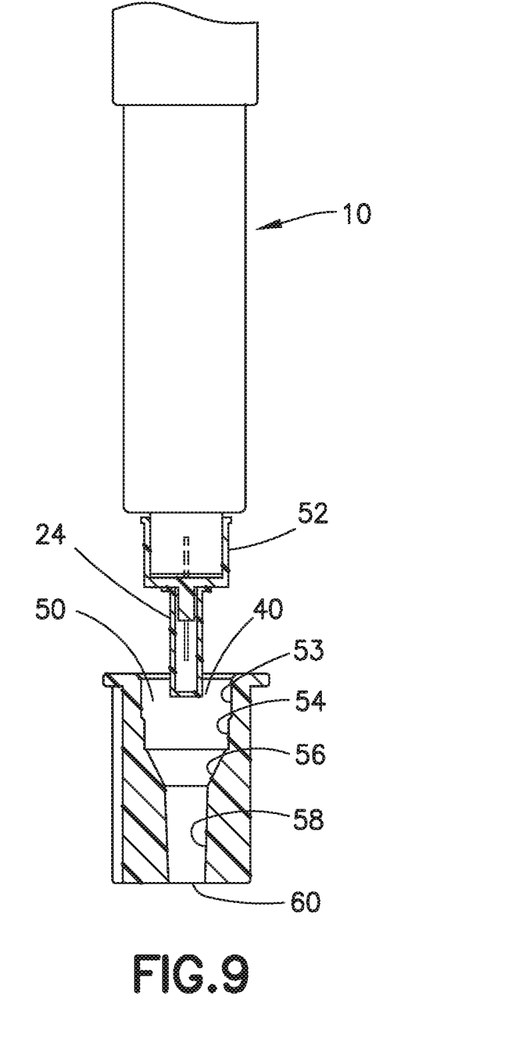
FIG. 9 is a cross-sectional view of the needle hub being removed from the outer cover.

Referring to FIG. 2, well 40 in outer cover 30 has a dimension to receive and support the needle hub 16 and inner shield 24 as a stand-alone assembly or package. As shown FIGS. 5 and 9, well 40 has a first portion 50 with a substantially annular or circular side wall 53 forming the well receiving the needle hub 16. In the embodiment show, needle hub 16 has a substantially cylindrical side wall 52 that mates with a circular side wall 53 of the first portion 50 of well 40. In one embodiment, side wall 53 of first portion 50 has a shape and dimension to engage the outer surface of side wall 52 to retain needle hub 16 within well 40 during storage and after use. In one embodiment, side wall 52 of well 40 can be formed with a longitudinally extending rib 54 as shown in FIG. 9 that can grip the outer surface of needle hub 16. Ribs 54 can be oriented to engage recesses formed in the outer wall 52 of needle hub 16 to resist rotation with respect to outer cover 30 for screwing delivery device 10 onto needle hub 16. In other embodiments, side wall 53 of well 40 can have a gradual taper to engage the outer surface 52 of needle hub 16. The open top end of the well 40 at the top face 36 can have a chamfered inner edge forming an inclined surface for assisting in inserting the used needle hub into the well 40. The engaging force between the side wall 53 and/or ribs 54 of the well 40 and the side wall 52 of the needle hub 16 can be a friction fit to retain needle hub within well 40. In other embodiments, the engaging force can be by an interference fit or other mechanical connection.

A conical shaped portion 56 extends from a bottom end of first portion 50 as shown in FIG. 9 to a longitudinally extending portion 58. In the embodiment shown, the longitudinally extending portion 58 has an open bottom end 60 at bottom face 38. In other embodiments, the bottom end portion 58 can be closed. Longitudinally extending portion 58 has a shape and dimension to receive the inner shield 24 in the original arrangement to maintain the cannula and needle hub in a clean and sterile condition. Longitudinally extending portion 58 can have gradual taper converging toward bottom face 38. Longitudinally extending portion 58 receives the inner shield without capturing the inner shield so that the inner shield remains connected to needle hub 16 when needle hub 16 is removed.

Figure 10:
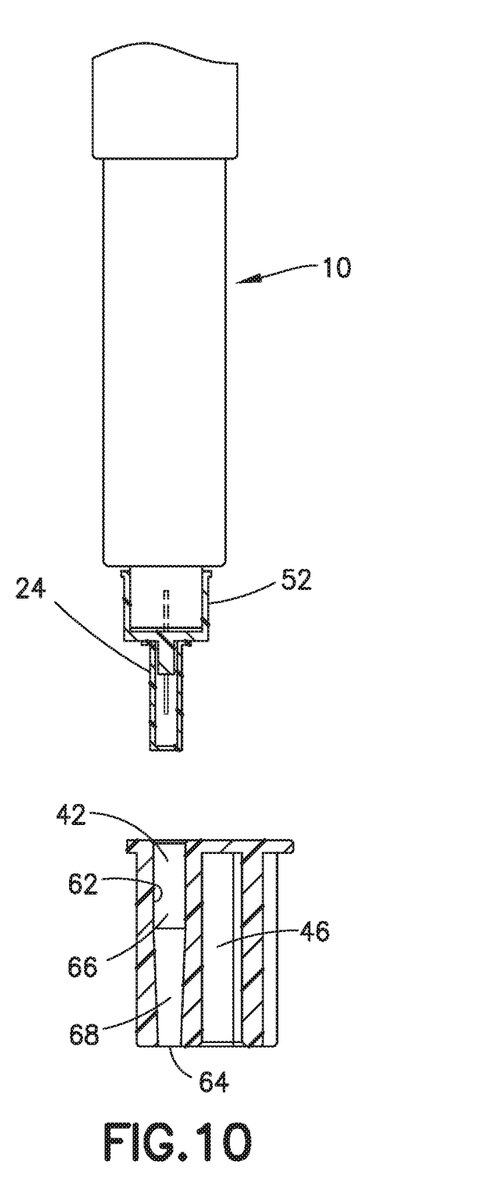
FIG. 10 is a cross-sectional view showing the needle hub positioned above the well for receiving the inner shield of the needle hub.

Second well 42 has a dimension and shape sufficient to receive and engage inner shield 24 in a manner where inner shield can be captured and retained within well 42 to separate inner shield 24 from pen needle delivery device 10. As shown in FIG. 10, well 42 has a longitudinal dimension with an inner wall 62 and an open bottom end 64. In the embodiment shown, inner wall 62 has a first substantially cylindrical portion 66 at a top end at top face 36 and a second tapered portion 68 converging toward bottom face 38. The tapered portion 68 forms a gripping face for engaging the outer surface of inner shield 24 when inserted into well 42. The open top end of the second well 42 at the top face 36 has a chamfered inner edge to assist in inserting the inner shield 24 into the well 42.

Figure 3:
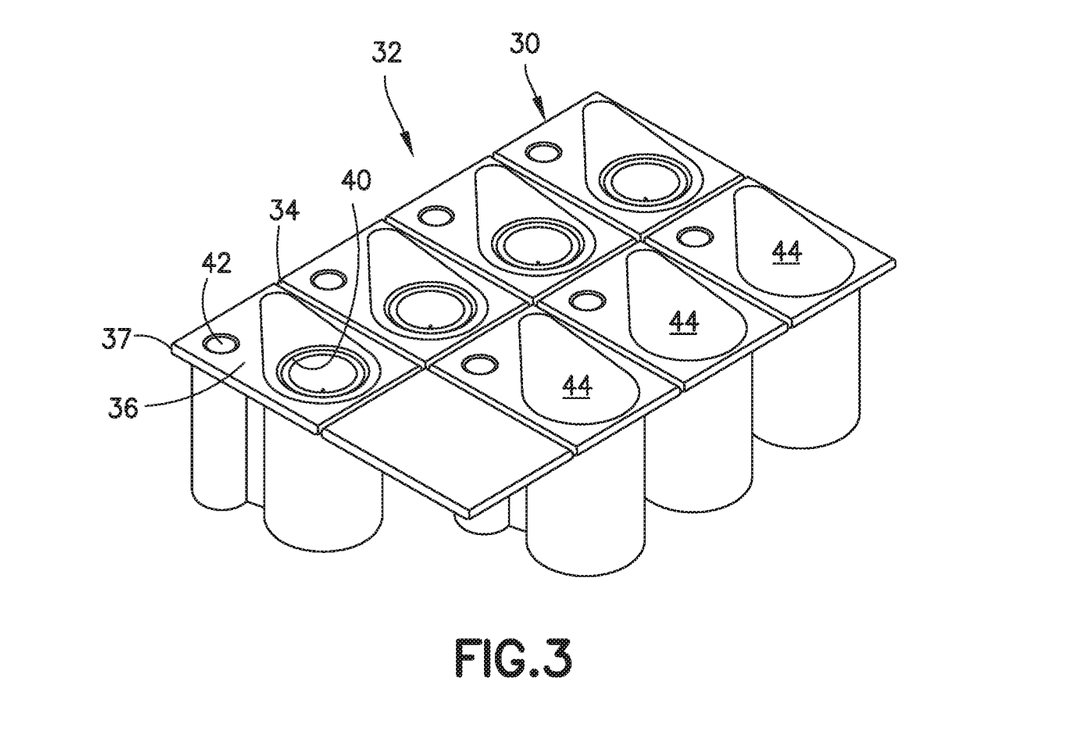
FIG. 3 is a perspective view of the array of FIG. 2.
Figure 4:
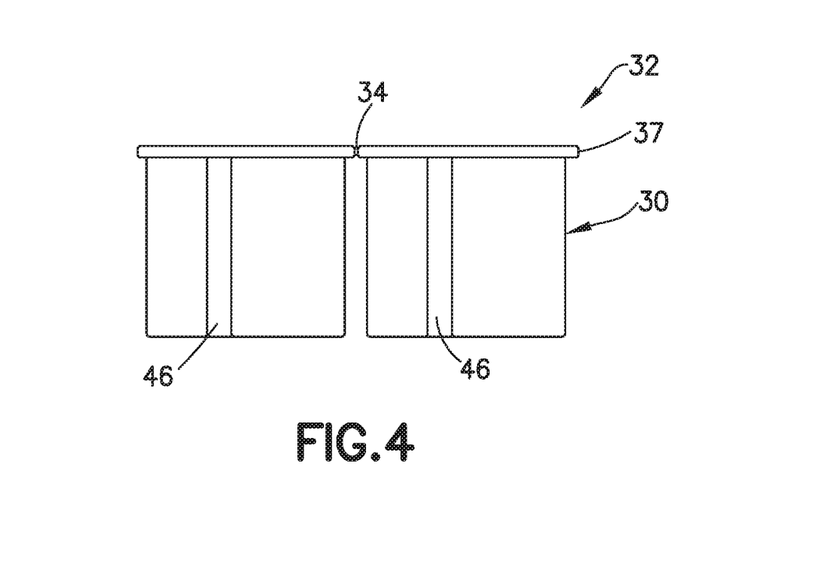
FIG. 4 is an end view of the array of FIG. 2.
Figure 5:
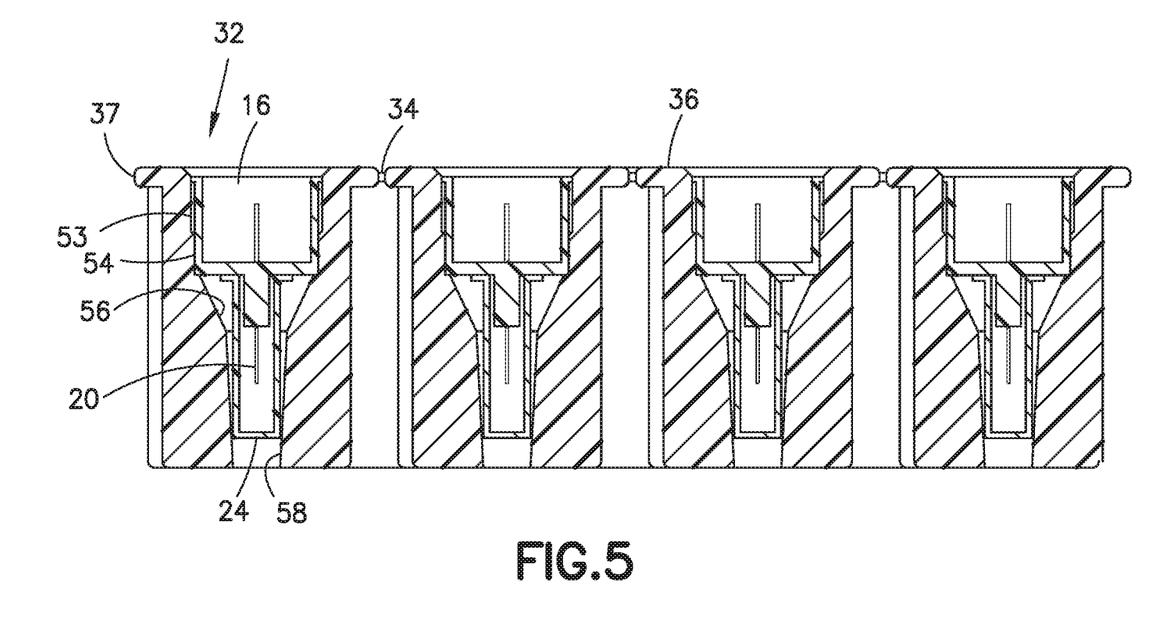
FIG. 5 is a cross-sectional view of the array pen needle hubs of FIG. 2.

The outer cover 30 contains the needle hub 16 as a packaged assembly to form the needle assembly that can be stored until ready for use. When needle hub 16 is ready for use, seal 44 is peeled from outer cover 30 and/or the needle hub 16 to expose well 40 and needle hub 16 contained in the well 40. FIGS. 2 and 3 show the seals removed from each of the individual outer covers 30 although typically the seal is separated one at a time when a needle hub is needed for injecting a substance to the patient.

Figure 6:
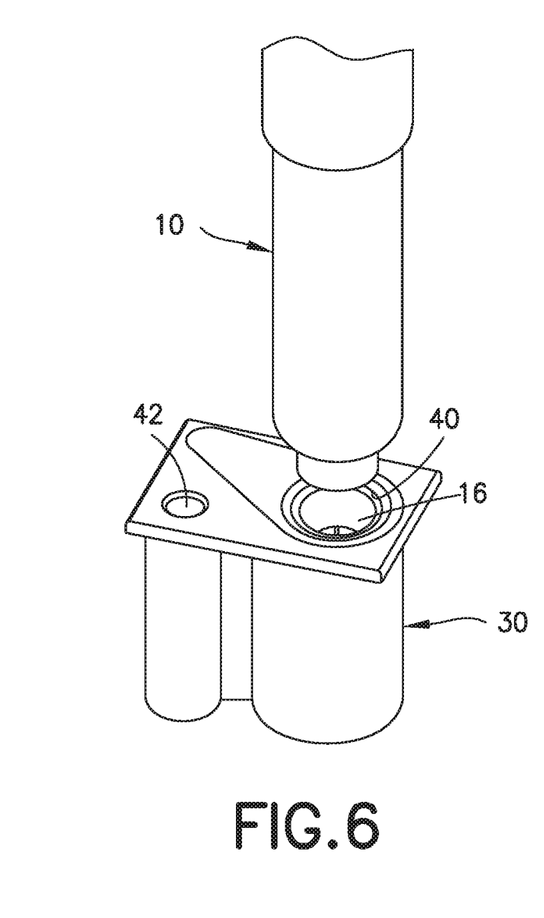
FIG. 6 is a perspective view of the pen needle delivery device positioned for coupling with a needle hub.
Figure 7:
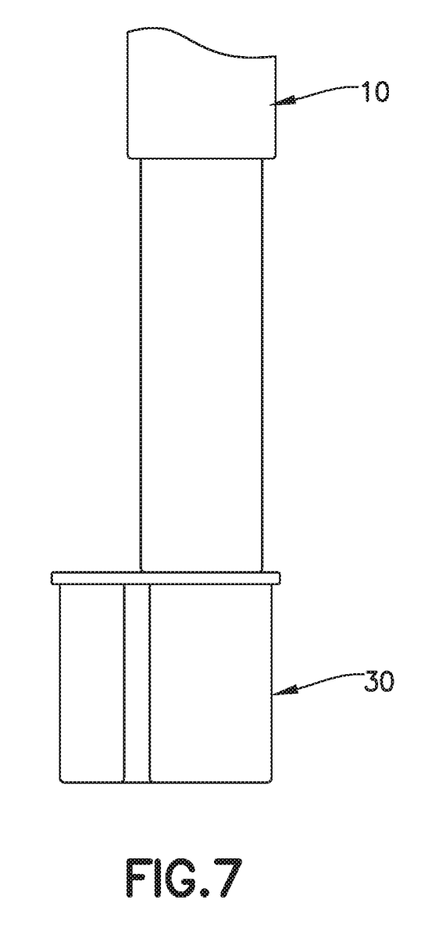
FIG. 7 is side view of the pen needle delivery device inserted into the outer cover.
Figure 8:
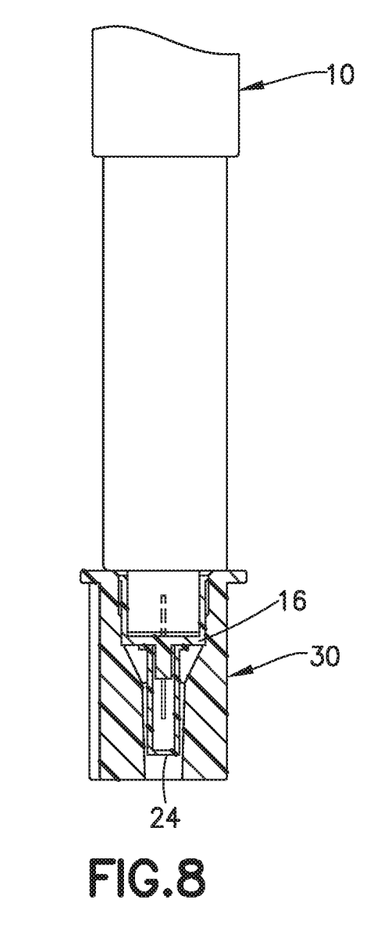
FIG. 8 is a cross-sectional view of the pen needle delivery device connected to the needle hub.

During use, as shown in FIGS. 6-8, the pen needle delivery device 10 is positioned over the open well 40 and inserted into the well 40 to couple the delivery device 10 to needle hub 16. In one embodiment, needle hub 16 is retained in well 40 by sufficient force so that the delivery device 10 can be coupled to the needle hub 16 with limited movement between the needle hub and the outer cover. Generally the coupling mechanism of the delivery device 10 has a threaded end that engages internal threads of the needle hub 16 as known in the art. The well 40 engages the needle hub 16 with sufficient force so that the delivery device 10 can be screwed onto the needle hub 16 while the needle hub 16 is retained in the well 40 with limited movement between the needle hub 16 and the outer cover 30.

Figure 11:
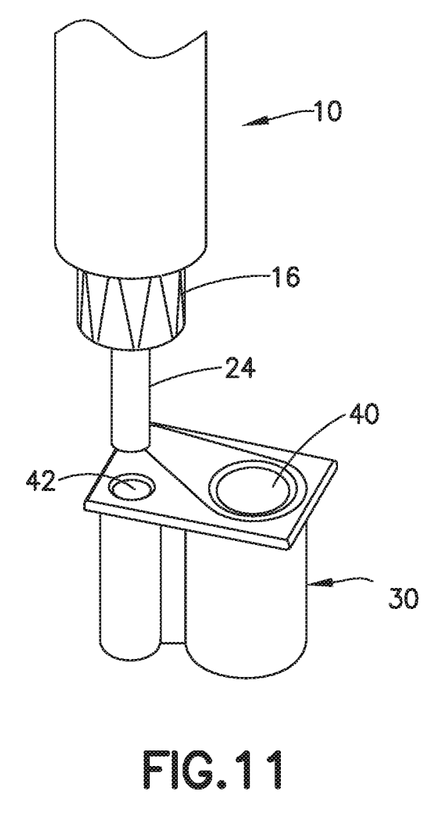
FIG. 11 is a perspective view showing the needle hub positioned above the well for receiving the inner shield.
Figure 12:
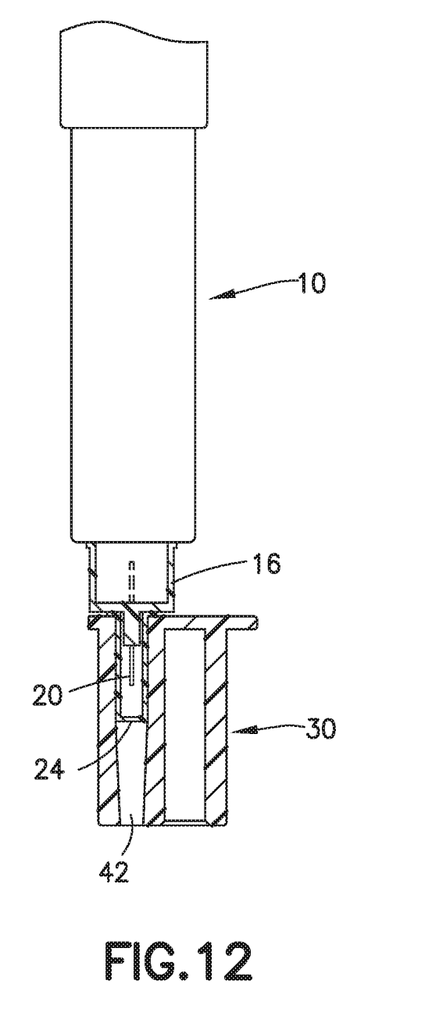
FIG. 12 is a cross-sectional view showing the inner shield positioned in the well.
Figure 13:
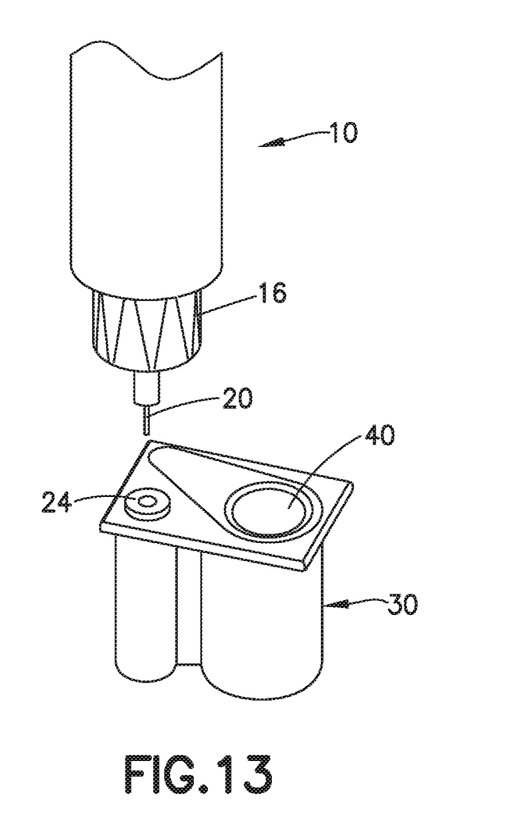
FIG. 13 is perspective view showing the needle hub separated from the inner shield.

After the delivery device is threaded onto the needle hub 16, the needle hub is withdrawn from the well 40 as shown in FIG. 9 with the inner shield 24 attached. The delivery device 10 is then positioned over the second well 42 with inner shield 24 aligned with well 42 as shown in FIGS. 10 and 11. The inner shield 24 is then inserted into the second well 42 as shown in FIG. 12 where the side wall of well 42 engages the outer surface of inner shield with sufficient force so that when pen needle delivery device 10 is pulled away from cover 30, inner shield 24 is retained within well 42. In this manner, the needle hub 16 can be connected to the delivery device 10 and the inner shield 24 can be separated from the post of the needle hub 16 without the need for the user to handle the cover or inner shield and with minimum exposure to the cannula and minimum risk of accidental needle stick. The delivery device with the attached needle hub 16 shown in FIG. 13 is ready for use to inject and deliver the substance to the patient.

Figure 14:
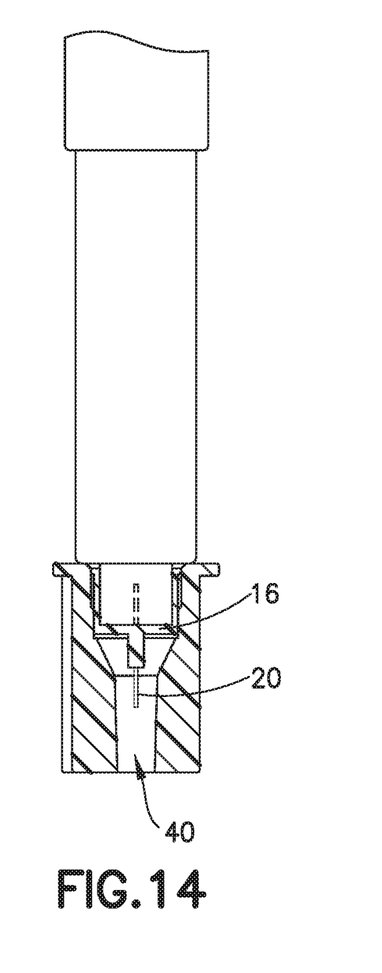
FIG. 14 is cross-sectional view showing the used needle hub inserted into the well.
Figure 15:
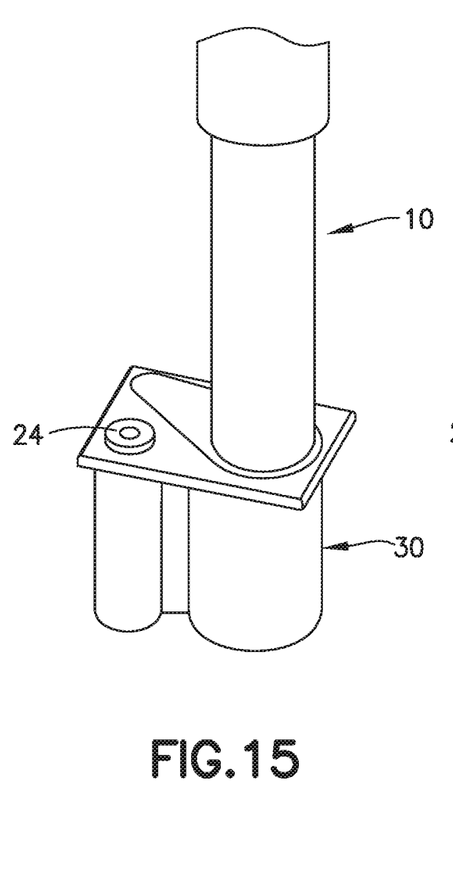
FIG. 15 is perspective view showing the used needle hub inserted into the well.
Figure 16:
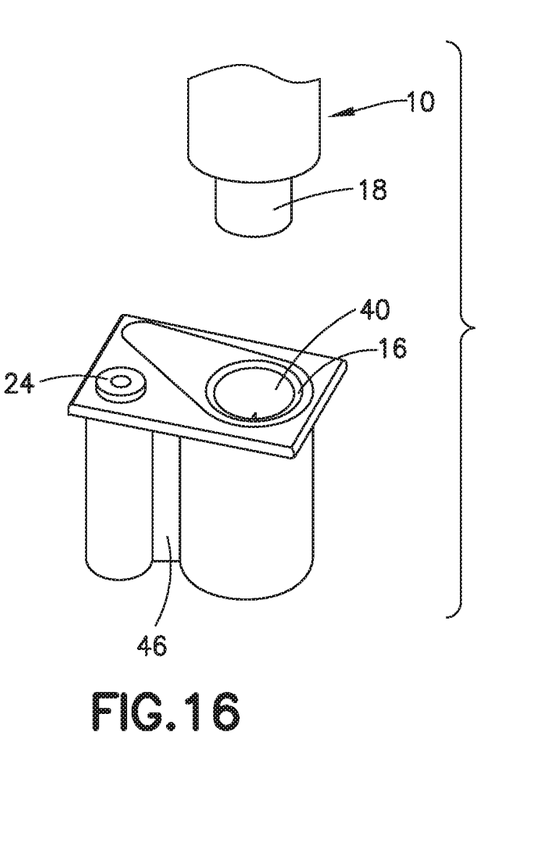
FIG. 16 is a perspective view showing the pen needle delivery device separated from the needle hub.
Figure 17:
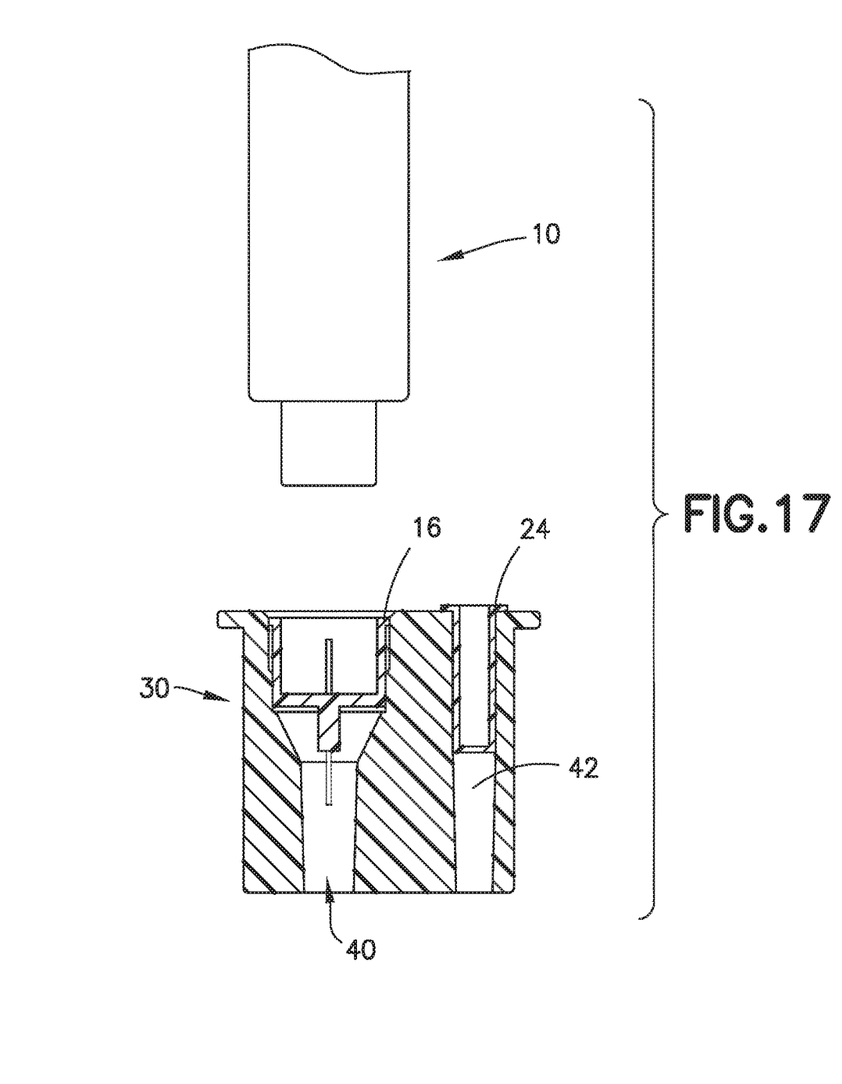
FIG. 17 is a cross-sectional view showing the pen needle delivery device separated from the used needle hub.

After the needle hub 16 is used, it is necessary to discard the used needle hub in a safe manner. As shown in FIG. 14, the used needle hub 16 while still attached to the delivery device 10 is inserted back into the well 40 where the needle hub 16 is gripped by sufficient pressure to enable the delivery device 10 to be separated from the used needle hub 16. In this embodiment, the delivery device 10 can be unscrewed from the needle hub 16. The delivery device 10 is then separated from the needle hub 16 as shown in FIGS. 16 and 17. As shown in FIG. 17, the used needle hub 16 and the inner shield 24 are retained within the respective wells 40 and 42 after use. The delivery device 10 can then be used again by coupling to a clean, unused needle hub 16. The outer cover 30 retaining the used needle hub 16 and inner shield can then be discarded in a safe location. The needle hub 16 is preferably retained within the well of the outer cover for proper disposal. The outer cover 30 with the respective needle hub 16 and inner shield 24 can be separated from the array 32 and discarded individually. Alternatively, each needle hub can be used and returned to the respective well and the array discarded as unit when all the needle hubs are used.

It will be appreciated by those skilled in the art that changes may be made to the embodiments described herein without departing from the scope of the invention. It is particularly noted that the features of different embodiments and claims may be combined with each other as long as they do not contradict each other. All such changes and combinations are considered to be within the scope of the invention, which is defined by the appended claims and their equivalents.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives, and variations will be apparent to those of ordinary skill in the art, and are intended to fall within the scope of the invention.

The invention claimed is:

1. A needle hub assembly for a pen needle delivery device, said assembly comprising:
    an outer cover having a bottom face with a configuration and dimension for contacting a support surface and retaining said outer cover in an upright orientation, and a top face opposite said bottom face, said top face having a first open well with a dimension for receiving a needle hub having a cannula extending from an end of said needle hub;
    an inner shield coupled to said needle hub and covering said cannula; and
    said top face having a second open well smaller than said first open well with a dimension and configuration for receiving said inner shield, where said inner shield is retained by inserting said inner shield into said second well whereby said inner shield can be separated from said needle hub.

2. The needle hub assembly of claim 1, further comprising a removable seal attached to said top face to close the first well.

3. The needle hub assembly of claim 1, wherein said seal is attached to said top face of said outer cover and to an open end of said needle hub.

4. The needle hub assembly of claim 2, wherein said seal is attached to said top face by an adhesive.

5. The needle hub assembly of claim 2, wherein said seal is a peelable label.

6. The needle hub assembly of claim 1, further comprising a plurality of said outer covers coupled together in an array and where each said outer cover includes a needle hub.

7. The needle hub assembly of claim 6, wherein said plurality of outer covers are separated from each other by a frangible line extending between adjacent outer covers.

8. The needle hub assembly of claim 1, wherein said first well has a dimension to receive said needle hub and inner shield, and where said first well engages said needle hub to enable coupling of said needle hub to a delivery device and where said needle hub and inner shield can be separated from said first well after coupling to said delivery device.

9. A needle hub array for use with a pen needle delivery device, comprising:
- a plurality of outer covers coupled together, each outer cover having a bottom face with a dimension and configuration for contacting a support surface and retaining said outer cover in an upright orientation, and a top face opposite said bottom face, said top face having a first open well with a first dimension and a second well with a second dimension smaller that said first dimension; and
- a needle hub received in each first well, said needle hub having a cannula extending from an end of said needle hub and an inner shield covering said cannula, where said outer cover encloses said needle hub and inner shield, said first open well in said top face having a dimension for receiving said needle hub and inner shield, and said second open well having a dimension and configuration for receiving said inner shield, where said inner shield is retained by inserting said inner shield into said second well.

10. The needle hub array of claim 9, wherein each said outer covers include a closure member closing said first well.

11. The needle hub array of claim 10, wherein said closure member is a removable seal attached to said top face to close said first well.

12. The needle hub array of claim 9, wherein said outer covers are separable from each other.

13. The needle hub array of claim 9, wherein said outer covers are separable by a frangible line extending between adjacent outer covers.

14. The needle hub array of claim 9, wherein said first well has a first portion with a dimension to receive and retain said needle hub by a friction fit, and a second portion having a dimension to receive said inner shield.

15. The needle hub array of claim 14, wherein said second well has a dimension to receive and retain said inner shield by a friction fit.

16. The needle hub array of claim 14, wherein said first well and said second well have an open bottom end at said bottom face of said cover.

17. The needle hub array of claim 9, further comprising a connecting portion extending between said first well and said second well and having a bottom edge at said bottom face of said outer cover to stabilize said outer cover.

18. A method of coupling and uncoupling a needle hub with respect to a pen needle delivery device for delivering a substance to a patient, said method comprising the steps of:
- providing an outer cover having a first well receiving the needle hub;
- inserting the pen needle delivery device into said first well and coupling to a coupling end of said needle hub;
- removing said pen needle delivery device and needle hub from said first well;
- inserting an inner shield coupled to said needle hub into a second well of said outer cover, where said second well is spaced from said first well, where said inner shield is gripped by said second well, and separating said needle hub from said inner shield for use in delivering the substance to the patient; and
- positioning the resulting used needle hub in said first well and uncoupling said needle hub from said pen needle delivery device.

19. The method of claim 17, wherein said outer cover includes a removable seal covering said first well and needle hub, and said method comprises removing said seal before inserting said pen needle delivery device into said first well.

* * * * *